United States Patent [19]

Thompson et al.

[11] 4,431,425
[45] Feb. 14, 1984

[54] FLOW FAULT SENSING SYSTEM

[75] Inventors: Thomas C. Thompson, McKinney; Martyn S. Abbott, Garland; Robert L. Easley, Plano, all of Tex.

[73] Assignee: Quest Medical, Inc., Carrollton, Tex.

[21] Appl. No.: 258,362

[22] Filed: Apr. 28, 1981

[51] Int. Cl.³ ............................................. A61M 5/00
[52] U.S. Cl. ................................... 604/246; 73/269; 137/486; 128/DIG. 13; 604/65; 604/245; 340/611; 340/686
[58] Field of Search .......... 128/214 R, 214 E, 214 F, 128/214.2, DIG. 12, DIG. 13, 634; 137/486, 487.5; 73/269-271; 340/556, 611, 626, 621, 606, 686; 604/65-67, 245, 246

[56] References Cited

U.S. PATENT DOCUMENTS

| | | | |
|---|---|---|---|
| 2,672,601 | 3/1954 | Welby | 340/686 |
| 2,948,890 | 8/1960 | Barth et al. | 340/686 X |
| 3,044,663 | 7/1962 | Norton et al. | 128/214 E X |
| 4,114,144 | 9/1978 | Hyman | 128/214 E |
| 4,201,222 | 5/1980 | Haase | 128/634 |
| 4,204,538 | 5/1980 | Cannon | 128/214 F |
| 4,207,871 | 6/1980 | Jenkins | 128/214 R |
| 4,315,523 | 2/1982 | Mahawili et al. | 73/269 X |

FOREIGN PATENT DOCUMENTS 2266522 10/1975 France ................ 128/214 E

*Primary Examiner*—Dalton L. Truluck
*Attorney, Agent, or Firm*—Richards, Harris & Medlock

[57] ABSTRACT

A system for sensing flow faults in a membrane system for intravenous fluid introduction is provided. A scanner is pulsed to generate reflected energy signals representative of the position of a membrane within a chamber. The scanner is pulsed both before and after the membrane is commanded to move within the chamber. The signals are then compared by an electronic circuit to determine the difference between them. If there exists a sufficiently large difference between the signals, this indicates that the membrane is moving in response to the command signals and the system is functioning properly. If there exists little or no difference between the signals, this indicates that there is a flow fault in the system, and an alarm is sounded.

8 Claims, 7 Drawing Figures

FLOW FAULT SENSING SYSTEM

TECHNICAL FIELD

This invention relates to membrane systems for intravenous fluid introduction, and more particularly to a sensing system for determining flow faults within the membrane system.

BACKGROUND ART

In the practice of medicine it is often desirable to introduce an intravenous fluid into a patient. The rate of introduction of the fluid to the patient is dependent upon a number of different factors including the weight, age, sex, physical state of the patient, and nature of the fluid to be introduced. Thus, in systems adapted for intravenous fluid introduction the rate of fluid introduction to the patient should be adjustable and measurable to assure that the patient receives an optimum benefit from the fluid. A very desirable feature of any such system is the automatic sensing of flow faults, i.e., situations where fluid is not being properly administered to the patient.

In copending application Ser. No. 258,361, filed concurrently by Thomas C. Thompson for an "Intravenous Drug Additive Delivery System with Electronic Control" and assigned of record to the assignee of record of this application, a system is disclosed and claimed for providing the introduction of intravenous fluid on a precisely controlled gravitational basis to a patient. Disposable cassettes are used in connection with apparatus to control the flow rate of intravenous fluid. The replaceable cassette has a cassette input line and a cassette output line which are connected to a source of fluid and the patient respectively. The cassette is manufactured of transparent plastic having various passageways and a membrane chamber molded therein. A flexible diaphragm membrane is disposed within the chamber to define a right and left side of the chamber. As the volume of one of the sides of the chamber is increased by movement of the membrane, the volume of the other side is correspondingly decreased. Each side of the chamber has an inlet and outlet line. The right and left inlet lines communicate with the cassette input line, and the right and left outlet lines communicate with the cassette output line.

Both inlet lines and both outlet lines are controlled by independently operable valves. The valves are operated alternately to allow periodic flow of fluid to the patient. For example, the inlet line to the left-hand side of the chamber is opened and the outlet line of the right-hand side of the chamber is opened, while the other two valves are closed, such that fluid flows from the right side of the chamber into the patient and into the left side of the chamber from the fluid source. Alternately, the inlet line of the right side of the chamber and the outlet line of the left side of the chamber are opened, the other valves now being shut, such that fluid flows into the patient from the left side of the chamber and from the fluid source into the right side of the chamber.

The opening and closing of the four valves is controlled by a microprocessor to produce a given flow rate into the patient. In one embodiment the flow rate has a range of 1 to 300 milliliters per hour. In the preferred embodiment, the chamber has a volume of one-tenth of a milliliter. Therefore, at a flow rate of 300 milliliters per hour the membrane shifts from one side of the chamber to the other side every 1.2 seconds. At a flow rate of one milliliter per hour the membrane shifts once every six minutes. Thus, the system disclosed and claimed in application Ser. No. 258,361 is advantageous because the cassette meters fluid by alternately shifting a membrane in a chamber such that one side of the chamber is filled while the other side is emptying and vice versa. The flow rate is directly controlled by the timing of the opening and closing of the valves associated with the chamber. No provision is made for the sensing of flow faults.

A somewhat similar system for intravenous introduction of a fluid is disclosed in U.S. Pat. No. 4,204,538 to Cannon. In Cannon, a multi-part cassette forming a chamber divided by a flexible membrane is shown. Four valves are provided to control the opening and closing of the inlet and outlet lines for each side of the chamber. However, in Cannon the membrane is directly attached to a ferrous rod which moves within a coil to produce a signal indicative of the position of the membrane within the chamber. The opening and closing of the various valves is controlled by sensing the position of the membrane by the ferrous rod transducer. When the transducer indicates that the membrane has reached its furthest extension in one direction, the valves are switched into the alternate configuration to begin the movement of the membrane in the direction of the other furthest extension. The line to the patient is constricted by a clamp downstream from the cassette. The constriction of the clamp is variable to produce different flow rates. The periodic switching of the valves in response to a control intelligence plays no part in the setting of the flow rate in Cannon. Further, the physical attachment of the position-sensing transducer to the membrane severely limits the dynamic range of the membrane. No flow fault sensing is provided in Cannon.

In U.S. Pat. No. 4,207,871 to Jenkins, flow rate, as opposed to flow fault, sensing is provided in a membrane system. The ferrous rod transducer of Cannon is excited by an oscillator to produce a signal which varies with the position of the membrane. The signal is integrated to determine the actual flow rate of the system. This flow rate is compared to the desired flow rate to generate a feedback signal to be applied to the clamp downstream. The flow rate is controlled in this manner, but no provision is made for sensing a flow fault in the system. Like in the Cannon system, the transducer in the Jenkins system severely limits the dynamic range of the membrane.

In systems of the type described above, the proper functioning of the system is entirely dependent on the back and forth movement of the membrane. If the membrane cannot or will not move for some reason, such as a ruptured membrane or any valve not functioning properly, the system will cease delivery of the fluid to the patient. The quick identification and repair of such a flow fault is necessary for the proper treatment of the patient, and thus a need has arisen for a system to determine and indicate such flow faults.

DISCLOSURE OF THE INVENTION

In accordance with the present invention, a system is provided to sense the movement of a flexible membrane and sound an alarm if the membrane is not moving in response to commands from a flow rate-setting microprocessor. The system includes an optical scanner, ultrasound scanner or the like positioned adjacent the membrane chamber to generate a signal and receive signals reflected back to it from the membrane. The scanner is pulsed to measure energy reflecting from the membrane by the microprocessor which controls the opening and closing of valves which cause the movement of the membrane within the chamber. The pulses are scheduled relative to the command signals to move the membrane from the microprocessor such that reflected signals from the membrane at both extremes of the chamber may be compared. An electronic circuit is provided to store and hold the values of reflected signal from the sensor that correspond to the extremes of membrane movement. An alarm is sounded if it is determined that the membrane has not moved when it should have. The sensing system does not require physical attachment to the membrane, and thus the dynamic range of the membrane is not effected by the system.

BRIEF DESCRIPTION OF THE DRAWINGS

A more complete understanding of the invention and its advantages will be apparent from the following detailed description taken in conjunction with the accompanying Drawings in which.

DETAILED DESCRIPTION

Figure 1:
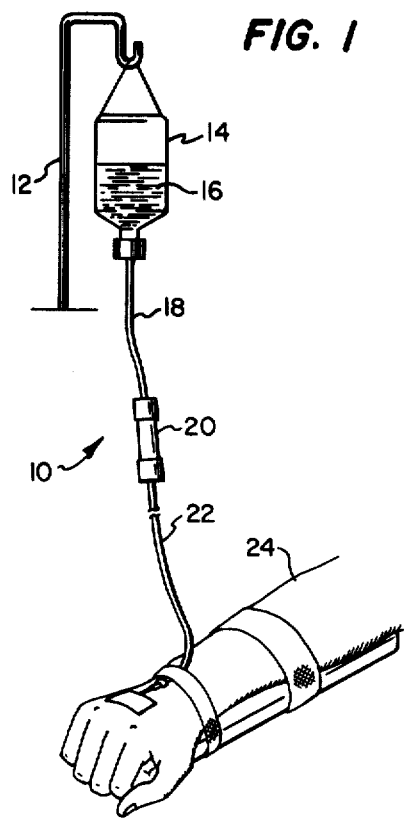
FIG. 1 is a view of a system for introducing intravenous fluid into a patient.

In FIG. 1 a typical intravenous fluid system 10 is illustrated having stand 12 and bottle 14. Fluid 16 can be a variety of different fluids, including for example, blood, saline solution and lipid solutions. Fluid 16 can be either transparent or opaque and can be any of a variety of colors including clear, white, yellow or red. Fluid 16 drains by gravity flow through line 18, cassette 20 and line 22 to arm 24.

Figure 2:
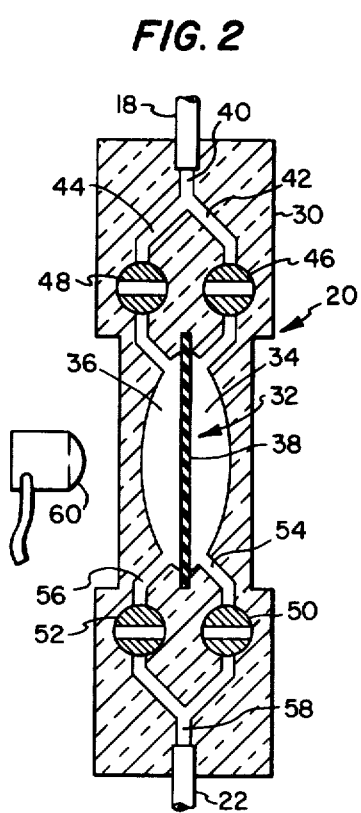
FIG. 2 is a diagrammatic view of a membrane system for intravenous fluid addition equipped for fluid fault sensing.

Referring now to FIG. 2, where certain features are enlarged, reduced, or symbolized for clarity of presentation, cassette 20 includes body 30 constructed of a transparent material such as clear polystyrene. A chamber 32 is provided within cassette 20 and is divided into right side 34 and left side 36 by membrane 38. Membrane 38 is constructed of a thin, flexible material such as silicone rubber. Line 18 is attached to the cassette and communicates with inlet passageway 40, which branches into right and left inlet passageways 42 and 44. Right inlet valve 46 and left inlet valve 48 are interposed in right and left inlet passageways 42 and 44 respectively. Right inlet passageway 42 communicates with right side 34 of chamber 32, and in like manner, left inlet passageway 44 communicates with left side 36. Right and left outlet valves 50 and 52 are interposed in right and left outlet passageways 54 and 56 respectively, which converge to form outlet passageway 58. Scanner 60 is disposed adjacent cassette 20 to sense the movement of membrane 38 as described below. Scanner 60 is equipped to generate and receive radiated energy signals such as light or sound waves. The energy spectrum embraced by the invention includes ultrasound and non-visible, e.g., infrared, light. In the preferred embodiment, scanner 60 is an integral optical scanner unit incorporating a receiver and a transmitter section, such as Model No. S27011 manufactured by SKAN-A-MATIC. An infrared diode in the package generates an infrared light signal. A short fiber optic receives light reflected from an object adjacent scanner 60 and transmits the light to a silicon diode which acts as a photo transducer. Scanner 60 passes current in an amount proportional to the amount of reflected light which it receives from an object adjacent to it when the infrared diode is energized.

Figure 3:
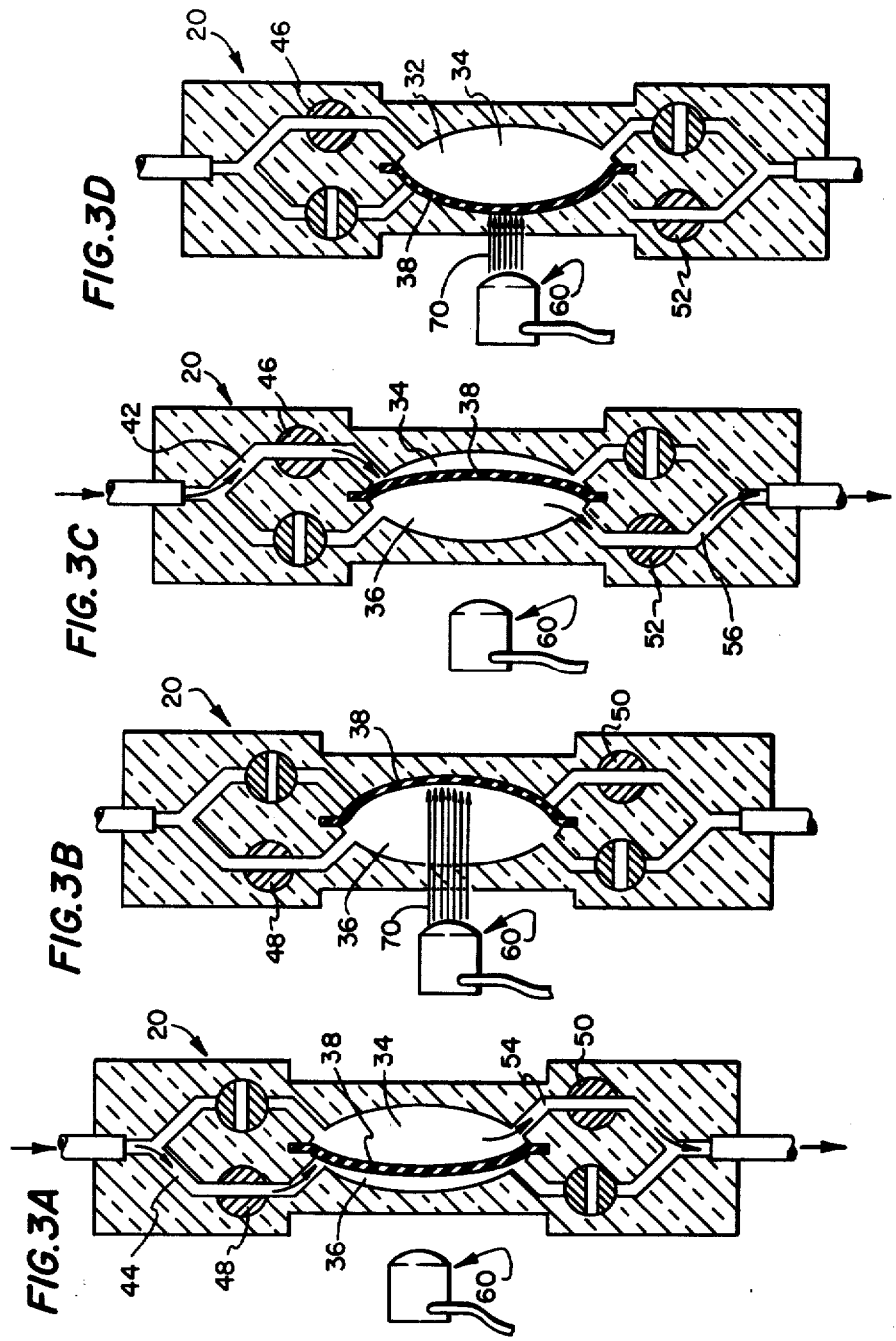
FIG. 3 is a representation of the operation of the present invention through one cycle of the system of FIG. 2 in four subviews, FIGS. 3A-3D.

Referring now to FIG. 3, subviews A-D illustrate a typical cycle of cassette 20 in the preferred embodiment including the flow fault sensing of the present invention. In FIG. 3A, left inlet valve 48 and right outlet valve 50 has just opened in response to a move right command signal from a control microprocessor (not shown). Fluid flows from right side 34 of the chamber through right outlet passageway 54 to the patient as indicated by the arrows as gravity causes the fluid to be admitted into the patient. Simultaneously, fluid from the bottle fills left side 36 of the chamber through left inlet passageway 44 as indicated by the arrows. When valves 48 and 50 are opened membrane 38 moves from left to right until it reaches the right contour of the chamber as shown in FIG. 3B. At that point, fluid flow to the patient ceases, the membrane comes to rest, and left side 36 of the chamber is full of fluid. The fluid in left side 36 will be delivered to the patient when the membrane begins to move back to the left in response to a move left command signal from the microprocessor. Prior to the signal to move left, however, it is desirable to pulse scanner 60 and obtain a reading of reflected light from the membrane. Light rays 70 are emitted from scanner 60 just before the command to move left is given. Rays 70 could equally represent sound waves in an embodiment of the invention comprising an ultrasound scanner. In FIG. 3C, a move left command signal has been received, valves 46 and 52 are open, and valves 48 and 50 are closed. Fluid drains from left side 36 through left output passageway 56 to the patient. Membrane 38 is moving from right to left as left side 36 empties and right side 34 is filled with fresh fluid from the bottle through right inlet passageway 42. In FIG. 3D, membrane 38 has moved all the way across chamber 32 to the left. At this point right side 34 is completely filled with fresh fluid. Fluid flow to the patient has ceased and will not resume until the move right signal from the microprocessor is given. At that point, the valves will be shifted to the arrangement shown in FIG. 3A to start a new cycle. In FIG. 3D it will be necessary to pulse scanner 60 to determine whether the membrane has moved after the move left signal was given. It may be desirable to pulse scanner 60 either shortly after the move left signal or immediately before the next move right signal is given, depending upon the flow rate as will be described below. In FIG. 3D, membrane 38 is much closer to scanner 60 as compared to its position in FIG. 3B, and therefore the reflected signal from the membrane in FIG. 3D is much greater than the signal received when the membrane is in the position shown in FIG. 3B. Thus, it can be seen that a difference in reflected energy received by the scanner from the membrane in the far right and far left positions indicates that the membrane has moved.

Figure 4:
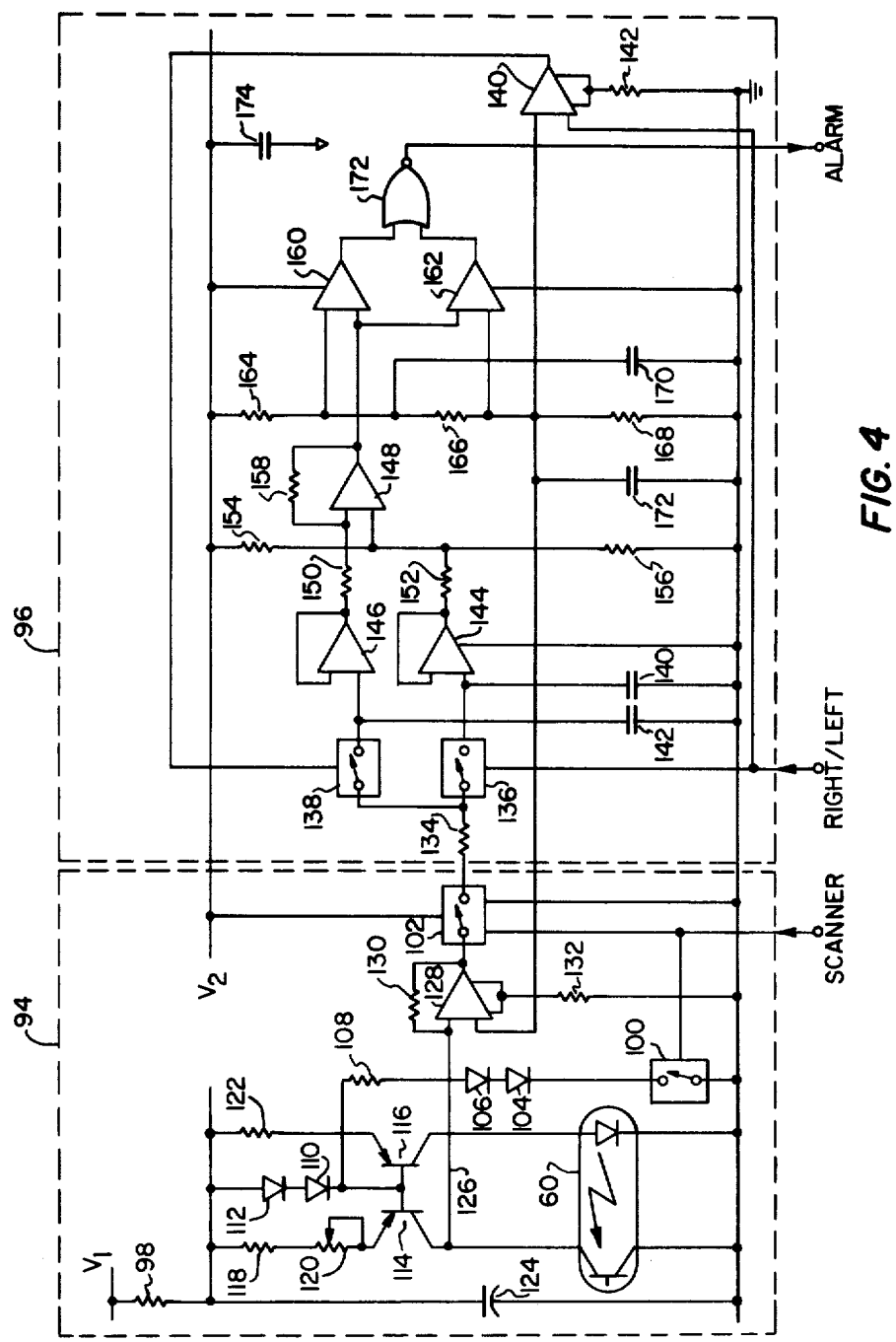
FIG. 4 is a circuit diagram of an electronic circuit which may be used with the present invention.

FIG. 4 is a circuit diagram of a circuit which may be used in the system of the preferred embodiment to activate the scanner and compare the signals generated by the scanner from reflected energy from the membrane in its right and left positions. An alarm is sounded if the reflected signals from the membrane before and after it is commanded to move are not sufficiently different.

The entire system is intended to be battery-operated, having two voltage supplies $V_1$ and $V_2$. The inputs to the system from the control microprocessor include an input marked "Scanner", which activates scanner 60 to generate a reflected signal, and an input marked "right-/left", which indicates whether the membrane is expected to be in either the left or right position. The output of the system, marked "Alarm", goes high when the circuit senses that the membrane has not moved after a command cycle. $V_1$ is the power supply for sensing circuit 94, which includes scanner 60, and $V_2$ powers the various logic elements in logic circuit 96.

In sensing circuit 94, the Scanner input is connected to the inputs of analog switches 100 and 102. $V_1$ is connected to sensing circuit 94 through resistor 98. Analog switch 100 is connected to resistor 98 through diodes 104 and 106, resistor 108 and diodes 110 and 112. $V_1$ is applied through diodes 110 and 112 to the bases of transistors 114 and 116 respectively. The emitter of transistor 114 is connected to $V_1$ through resistor 118 and potentiometer 120. The emitter of transistor 116 is connected to $V_1$ through resistor 122. The collector of transistor 116 is connected to the LED transmitter portion of scanner 60, which in the preferred embodiment is an optical scanner. The collector of transistor 114 is connected to the receiver portion of scanner 60 indicated by a transistor symbol. Capacitor 124 is connected across $V_1$ and ground. Line 126 connects the collector of transistor 114 and the negative input of inverting amplifier 128, which has feedback resistor 130 and bias-setting resistor 132. The output of amplifier 128 is applied to analog switch 102.

In operation, when the Scanner input goes high switch 100 is closed. Current flows through diodes 104 and 106, resistor 108, and diodes 110 and 112 thereby switching on transistors 114 and 116. When transistor 116 is on, current flows through the LED and scanner 60 produces a light signal. Th receiver portion of scanner 60 passes current in an amount proportional to the reflected light received from the membrane. Current passed by the receiver portion of the scanner reduces the current flowing through line 126. The amount of current flowing from transistor 114 into line 126 is thus inversely proportional to the current flowing through the receiver portion of scanner 60. Thus, the output of inverting input of amplifier 128 is proportional to the amount of light reflected from membrane 38 and received by scanner 60. Potentiometer 120 is used to set a threshold level of current to be passed through transistor 114. Scanner 60 is pulsed to converse the battery supply rather than operated continuously. While the LED is off, capacitor 124 is charged by $V_1$ through resistor 98. When the scanner is activated, a substantial portion of the power required to drive the LED is supplied by capacitor 124. This smooths the current draw on voltage source $V_1$.

When switch 102 is closed by a high Scanner input, the output of amplifier 128 passes through switch 102 to logic circuit 96 at resistor 134. The right/left input from the control microprocessor is switched on or off each time the membrane is commanded to move. Thus, for example, a high sighal at the right/left input could signify that the membrane should be on the right side of chamber 132, and a low signal could indicate a left side position of the membrane. Of course, this protocol could be reversed. The right/left signal is applied to switch 136 directly and to switch 138 through inverting amplifier 140. Inverting amplifier 140 includes bias-setting resistor 142. The output of switch 136 is applied to capacitor 140, and the output of switch 138 is applied to capacitor 142. Capacitors 140 and 142 are connected to buffers 144 and 146 respectively. The output of buffer 146 is applied to the negative input of subtracting amplifier 148 through resistor 150. The output of buffer 144 is applied to the positive input of subtracting amplifier 148 through resistor 152. The positive input of subtracting amplifier 148 is connected to $V_2$ and ground through resistors 154 and 156 respectively. Feedback resistor 158 is provided for use with subtracting amplifier 148.

The output of subtracting amplifier 148 is applied to the positive input of comparator 160 and the negative input of comparator 162. The negative input of comparator 160 is connected to the junction of resistors 164 and 166, and the positive input of comparator 162 is connected to the junction of resistors 166 and 168. The other lead of resistor 164 is connected to $V_2$, and the other lead of resistor 168 is connected to ground. Stabilizing capacitor 170 is connected between ground and the junction of resistors 164 and 166. Stabilizing capacitor 172 is connected between ground and the junction of resistors 166 and 168. The outputs of comparators 160 and 162 are connected to the inputs of NOR gate 172. The output of NOR gate 172 provides the Alarm output of the circuit. Stabilizing capacitor 174 is provided between $V_2$ and ground.

In operation, signals from sensing circuit 94 are applied to either capacitor 140 or 142 depending on the right/left signal applied to switches 136 and 138. If right/left signal is high, capacitor 140 is charged by current from sensing circuit 94, and if right/left signal is low, capacitor 142 is charged. Thus, the charge on capacitor 140 represents the energy reflected from membrane 38 in one position, right or left depending on the protocol chosen, and the charge on capacitor 142 represents the energy relfected from membrane 38 in the other position. The pulses to sensing system 94 are timed so that the charge on capacitors 140 and 142 represent the signal reflected by membrane 38 before and after it moves from position to the other. Thus, if there is a sufficiently large difference between the charges on the two capacitors, this will indicate that the membrane has indeed moved and that the system is operating correctly. The charge level from capacitors 140 and 142 are subtracted in comparator 148, and the difference is added (or subtracted) from a reference voltage applied to the positive input of comparator 148 through resistors 152, 154 and 156. High and low reference voltages are applied to comparators 160 and 162 through resistors 164, 166 and 168, thus establishing a window for comparing the output comparator 148. As long as the output of 148 is either above the high reference voltage or below the low reference voltage, thereby indicating a sufficiently large difference between the charges on capacitors 140 and 142, the output of NOR gate 172 is low. However, if the output of comparator 148 is within the window of voltages, thereby indicating little or no difference between the charges on capacitors 142 and 140, NOR gate 152 causes the Alarm output to go high, indicating a flow fault to the control microprocessor. Thus it can be seen that an alarm is sounded if the system detects that the membrane has not moved when it should have. This is accomplished by taking readings of reflected energy from the membrane both before and after it has been commanded to move and storing these readings in capacitors 140 and 142. If the reflected energy signals are the same or close to one another before and after the membrane has been commanded to move, this indicates that the membrane has in fact not moved. An alarm is then activated. If, however, the reflected signals from before and after a command signal is given are sufficiently different, the alarm signal is silent, because this indicates that the membrane has moved and that the system is functional.

The timing of the scanner pulses may be important to the operation of the system of the present invention. In the preferred embodiment, chamber 32 has a volume of one tenth of one milliliter. At flow rates greater than 50 milliliters per hour, the membrane is moving from one side of the chamber to the other side in time periods less than 10 seconds. When the system is set to deliver fluid at a flow rate greater than 50 millimeters per hour, the scanner is pulsed to take a reading from the membrane immediately before the membrane is commanded to move. Thus, for example, immediately before the membrane is commanded to move left the scanner is pulsed to obtain a reading from the membrane in the right position. After the membrane has moved to the left position, and immediately before it is commanded again to move right, the scanner is pulsed to obtain a reading from a membrane in the left position. These readings are compared by a circuit such as that shown in FIG. 4 to determine if indeed the membrane has moved since the last command was given. The charge on storage capacitors 140 and 142 is maintained for comparison until just before the next command signal is given. As stated above, at flow rates greater than 50 milliliters per hour, the time during which charge must be maintained may be as long as 10 seconds.

In the preferred embodiment, which comprises an optical scanner, at flow rates less than 50 milliliters per hour leakage current from capacitors 140 and 142 impairs the operation of the system if the scanner is only pulsed immediately before the command signals as just described. Under these flow conditions, the membrane position is sensed immediately before the command signal is given and again approximately half a second after the command signal is given. These values are then compared to determine if the membrane has moved. Before the membrane is next moved, this sequence of pulses is repeated, one pulse immediately before the command signal and one pulse one-half second after the command signal. Thus the problem of leakage current is obviated at flow rates less than 50 milliliters per hour.

Variations in the reflectivity of fluids between the scanner and the membrane are accounted for by comparing the reflected signals from the membrane. A white opaque fluid such as a lipid solution will have a greater reflectivity of light than a dark opaque fluid such as blood. Thus, for example, for a lipid solution the current in line 126 from the sensing system may vary from between 14 and 16 microamps between right and left positions of the membrane. For blood, a relatively nonreflective fluid, the optical scanner signals might vary from between two to four microamps between membrane positions. Because the circuit of FIG. 4 detects the difference between the scanner signals, and not the ratio or an absolute value of signals, the variations in reflectivity between different fluids is accounted for. Comparing the reflected signals from the membrane also accounts for the dwindling of battery voltages with age.

The color of the membrane is important to the proper operation of embodiments of the invention that include an optical scanner. For example, red and pink membrane materials give the best results while yellow diaphragm materials are unsuitable.

While only one embodiment of the present invention has been described in detail herein and shown in the accompanying Drawings, it will be evident that various further modifications are possible without departing from the scope of the invention.

We claim:

1. A volumetric metering device for controlling the flow of fluid in a fluid path extending from a fluid supply to a patient which automatically and non-invasively senses flow faults comprising:
    (a) a metering chamber of predetermined volume much smaller than the volume of fluid to be delivered to the patient, divided into first and second compartments by a membrane, said first and second compartments each having an inlet and and outlet;
    (b) valve means settable into a first state in which the inlet to the first compartment and the outlet from the second compartment are open and the outlet from the first compartment and the inlet from the second compartment are closed; and a second state in which the inlet to the second compartment and the outlet from the first compartment are open and the inlet to the first compartment and the outlet from the second compartment are closed, whereby a small discrete volume of fluid equal to the volume of the chamber is delivered upon each alternate switching into the first or second state of the valve means;
    (c) control means for cycling the valve means by setting the time lapse between each successive setting of the valve means into such states; and
    (d) non-invasive flow fault sensing means external to the metering chamber for generating discrete signals the magnitude of which is directly determined by the position of the membrane during preselected portions of the cycling established by the control means, and for comparing such signals with each other to determine movement of the membrane.

2. A volumetric metering device for controlling the flow of intravenous fluid in a fluid path extending from a fluid supply to a patient which automatically and non-invasively senses a flow fault comprising:
    (a) a metering chamber divided into first and second compartments by a flexible membrane, said first and second compartments each having an inlet and an outlet;
    (b) valve means settable into a first state in which the inlet to the first compartment and the outlet from the second compartment are open and the outlet from the first compartment and the inlet from second compartment are closed; and a second state in which the inlet to the second compartment and the outlet from the first compartment are open and the inlet to the first compartment and the outlet from the second compartment are closed, whereby a discrete volume of fluid equal to the volume of the metering chamber is delivered to the patient upon switching into each such state of the valve means;
    (c) control means for causing delivery of fluid at a selected overall volumetric rate of fluid flow to the patient, although not an instantaneous flow rate, comprising means for switching the valve means into such states alternately at a predetermined constant time interval; and (d) non-invasive sensing and alarm means external to the metering chamber for generating reflected energy signals representative of the position of the membrane during preselected portions of the operation of the control means, and comparing such signals with each other to determine membrane movement.

3. A volumetric metering device for delivering an intravenous fluid to a patient through a fluid line in discrete increments, which automatically and noninvasively senses a flow fault, comprising:

(a) a metering chamber having a small predetermined volume divided into first and second compartments by a membrane, said chamber having valved inlet and outlet means;

(b) control means for switching the valve inlet and outlet means to cause the membrane to move and discrete increments of fluid to be delivered to the patient, each increment equal to the chamber volume;

(c) means external to the chamber for generating a first signal representative of membrane position prior to switching by the control means and a second signal representative of membrane position after such switching;

(d) comparator means for comparing the first and second signals; and (e) alarm means for producing a perceptible alarm in the event that the comparator means indicates that the membrane is not moving in response to the control means.

4. In a membrane system for intravenous fluid delivery employing a metering chamber separated into two compartments by a movable membrane, a flow fault sensing system comprising:

(a) means for producing reflected energy signals representative of the position of the membrane comprising a scanner which detects energy reflected from membrane; and (b) means for processing said signals to determine whether the membrane has moved in response to a command signal comprising means for comparing said reflected energy signals from said scanner.

5. The flow fault sensing system of claim 4 wherein said scanner is pulsed to generate a first reflected energy signal before the command signal and a second reflected energy signal after the command signal, said first and second reflected energy signals being compared by said means for comparing to determine the difference between said first and second signals.

6. An apparatus for intravenous introduction comprising:

a membrane enclosed by a body;

means for moving the membrane with respect to the body in accordance with cycle established by a control intelligence;

a transmitter of energy signals directed toward the membrane;

a receiver of energy signals reflected from the membrane;

means for pulsing the transmitter and receiver during selected portions of the cycle established by the control intelligence such that at least first and second reflected energy signals representative of the positions of the membrane at different times are received;

means for holding and interpreting a plurality of reflected energy signals to determine whether the membrane has moved in accordance with the control intelligence; and alarm means for producing a perceptible alarm in the event that the membrane has not moved in accordance with the control intelligence.

7. The apparatus of claim 6 wherein said means for holding and interpreting the signals includes means for determining the difference between the first and second reflected energy signals and means for comparing the difference to a reference to ascertain whether the membrane has moved.

8. The apparatus of claim 7 including a first storage member adapted to hold a first voltage representing the first energy signal, a second storage member adapted to hold a second voltage representing the second energy signal, means for ascertaining the difference between the first and second voltages; means for comparing the difference with a reference voltage; said alarm means being activated should the difference between the first and second voltages be insufficient to indicate that the membrane has moved.

* * * * *